(12) United States Patent
Brunfeld et al.

(10) Patent No.: US 7,330,277 B2
(45) Date of Patent: *Feb. 12, 2008

(54) RESONANT ELLIPSOMETER AND METHOD FOR DETERMINING ELLIPSOMETRIC PARAMETERS OF A SURFACE

(75) Inventors: Andrei Brunfeld, Cupertino, CA (US); Gregory Toker, Jerusalem (IL); Bryan Clark, Mountain View, CA (US)

(73) Assignee: Xyratex Technology Limited, Havant, Hampshire (GB)

( * ) Notice: Subject to any disclaimer, the term of this patent is extended or adjusted under 35 U.S.C. 154(b) by 111 days.

This patent is subject to a terminal disclaimer.

(21) Appl. No.: 11/156,309

(22) Filed: Jun. 17, 2005

(65) Prior Publication Data

US 2005/0225775 A1 Oct. 13, 2005

Related U.S. Application Data

(63) Continuation-in-part of application No. 10/644,243, filed on Aug. 20, 2003, now Pat. No. 7,022,978.

(60) Provisional application No. 60/583,342, filed on Jun. 28, 2004, provisional application No. 60/581,506, filed on Jun. 21, 2004.

(51) Int. Cl.
   *G01B 9/02* (2006.01)
(52) U.S. Cl. ...................... 356/519; 356/480
(58) Field of Classification Search ............... 356/480, 356/491, 519
   See application file for complete search history.

(56) References Cited

U.S. PATENT DOCUMENTS

| | | |
|---|---|---|
| 5,181,080 A | 1/1993 | Fanton et al. |
| 5,235,192 A | 8/1993 | Chase et al. |
| 6,522,471 B2 | 2/2003 | Clark |
| 6,653,649 B2 | 11/2003 | Clark |
| 6,700,840 B2 | 3/2004 | Clark |
| 6,714,295 B2 | 3/2004 | Clark |
| 6,717,707 B2 | 4/2004 | Clark |

(Continued)

OTHER PUBLICATIONS

Holzapfel et al, Intercavity transmission ellipsometry for optically anisotropic components, Applied Optics, Oct. 1993, vol. 32, No. 30, pp. 6022-6032.*

Jacob et al, Pulsed measurement of high-reflectivity mirror phase retardances, Applied Optics, May 1994, vol. 33, No. 15, pp. 3175-3178.*

(Continued)

*Primary Examiner*—Samuel A. Turner
(74) *Attorney, Agent, or Firm*—Mitch Harris, Atty at Law, LLC; Andrew M. Harris

(57) ABSTRACT

A resonant ellipsometer and method for determining ellipsometric parameters of a surface provide an efficient and low-cost mechanism for performing ellipsometric measurements. A surface of interest is included as a reflection point of a resonance optical path within a resonator. The intersection of the resonance optical path with the surface of interest is at an angle away from normal so that the complex reflectivity of the surface alters the phase of the resonance optical path. Intensity measurements of light emitted from a partially reflective surface of the resonator for orthogonal polarizations and for at least two effective cavity lengths provide complete information for computing the ellipsoidal parameters on the surface of interest. The resonator may be a Fabry-Perot resonator or a ring resonator. The wavelength of the illumination can be swept, or the cavity length mechanically or electronically altered to change the cavity length.

21 Claims, 7 Drawing Sheets

U.S. PATENT DOCUMENTS

| | | |
|---|---|---|
| 6,774,997 B2 | 8/2004 | Rosencwaig et al. |
| 6,778,307 B2 | 8/2004 | Clark |
| 6,879,421 B2 | 4/2005 | Clark et al. |
| 6,897,955 B2 | 5/2005 | Wielsch et al. |
| 6,927,864 B2 | 8/2005 | Clark |
| 7,022,978 B2 | 4/2006 | Clark et al. |
| 7,102,740 B2 | 9/2006 | Clark et al. |
| 7,214,932 B2 * | 5/2007 | Brunfeld et al. ............ 356/450 |

OTHER PUBLICATIONS

U.S. Appl. No. 11/143,018, filed Jun. 1, 2005, Brunfeld et al.
U.S. Appl. No. 11/169,517, filed Jun. 29, 2005, Brunfeld et al.
U.S. Appl. No. 11/167,807, filed Jun. 27, 2005, Brunfeld et al.
U.S. Appl. No. 11/149,094, filed Aug. 8, 2005, Toker et al.
U.S. Appl. No. 10/770,866, filed Feb. 4, 2004, Brunfeld et al.

* cited by examiner

RESONANT ELLIPSOMETER AND METHOD FOR DETERMINING ELLIPSOMETRIC PARAMETERS OF A SURFACE

CROSS-REFERENCE TO RELATED APPLICATIONS

This application is related to U.S. Provisional Patent Applications: "Polarization-Enhanced Fabry Perot Detection", Ser. No. 60/581,506 and "Ellipsometric Optical Resonators and Ellipso-Height Topography", Ser. No. 60/583,342 filed by the same inventors on Jun. 21, 2004 and Jun. 28, 2004, respectively, from which benefit under 35 U.S.C. §119(e) is claimed. The present application is also a Continuation-in-Part of U.S. patent application Ser. No. 10/644,243 issued as U.S. Pat. No. 7,022,978 on Apr. 4, 2006, entitled "METHOD AND APPARATUS INCLUDING IN-RESONATOR IMAGING LENS FOR IMPROVING RESOLUTION OF A RESONATOR-ENHANCED OPTICAL SYSTEM", which was filed on Aug. 20, 2003 having at least one common inventor and assigned to the same assignee, the specification of which is incorporated by reference. The present application is also related to U.S. patent applications: Ser. No. 11/143,018 entitled "FABRY-PEROT RESONATOR APPARATUS AND METHOD FOR OBSERVING LOW REFLECTIVITY SURFACES", filed on Jun. 1, 2005 and Ser. No. 11/149,094 entitled "FABRY-PEROT RESONATOR APPARATUS AND METHOD INCLUDING AN IN-RESONATOR POLARIZING ELEMENT", filed on Jun. 8, 2005 by the same inventors and assigned to the same Assignee, the specifications of which are incorporated herein by reference.

BACKGROUND OF THE INVENTION

1. Field of the Invention

This invention relates to optical systems, and more specifically, to an ellipsometric optical measurement system incorporating a resonator to enhance the resolution and sensitivity of the system.

2. Description of the Related Art

Resonator-enhanced optical inspection systems, storage devices and other optical systems, such as those described by U.S. Pat. Nos. 6,653,649, 6,700,840, 6,714,295, 6,717,707, 6,778,307 issued to Applicant Clark and others, the specifications of which are incorporated herein by reference, provide improved resolution, surface detection and other performance improvements in traditional optical systems and provide new types of optical systems that were not available prior to the inventions disclosed therein.

In particular, the combination of a partially reflective surface with a surface under measurement to form a Fabry-Perot resonator provides increased resolution, improved differentiation of surface height and differentiation of surface characteristics, and improved feature detection over the prior available techniques.

However, the reflection measurement systems disclosed in the above-referenced U.S. patents are generally directed toward surface measurements that center on the performance of the surface of interest and other reflectors as ideal reflectors. As such, significant surface feature characteristics, such as transmission vs. absorption and polarization changing effects are not detected by such systems, or their effect is essentially combined with other effects, so that the additional surface characteristics are not uniquely detected. When transmission or absorption characteristics are measured, such as in above-incorporated U.S. Pat. No. 6,653,649, they are combined in the total reflected amplitude or phase at the Fabry-Perot external detection surface and are limited to determining specific characteristics, such as the thickness of a refracting layer.

Ellipsometry is a well-known technique for measuring the complex reflection characteristics of a surface, which provide information about material and structure of a surface. Ellipsometry is also used for thin-film layer investigation, where multiple thin film layers yield complex reflective changes. By controlling the polarization of light directed at a surface at a non-normal incidence angle and then variably filtering the reflected light for a particular polarization angle or interfering the reflected polarizations, the polarizing effect of the surface at the particular angle of incidence can be mapped by finding the minimum and maximum amplitude points as the receive filter is rotated. The mapping is performed over several angles of incidence on the surface, and the complex refractive index components (n—index of refraction) and (k—extinction coefficient) can be determined from the "ellipsometric parameters" which is the phase angle and the ratio of the refractive indices at the surface boundary.

The ellipsometric detection can be performed by rotating a polarizer to determine the major axis and minor axis of an amplitude ellipse that describes the polarization behavior, or by interfering two orthogonal polarization states of the reflected beam, as in a Beam Profile Ellipsometer (BPE) such as that described in U.S. Pat. No. 5,181,080 to Fanton, et al. The measurements are typically performed over several incidence angles in order to determine the complex surface reflectivity.

However, standard ellipsometers are limited by the resolution of the system, the phase sensitivity of an interferometric measurement and/or the accuracy of the amplitude-based "manual" ellipse technique described above.

It would therefore be desirable to improve the performance of an ellipsometer by increasing its sensitivity and resolution. It would also be desirable to add polarization measurement capability to optical systems disclosed in the above-referenced patents, as well as other resonator-enhanced optical systems, in order to provide measurement of complex optical surface properties or detection of surface features that generate changes in such optical properties. It would finally be desirable to detect ellipsometric parameters of a surface in an efficient and rapid manner.

SUMMARY OF THE INVENTION

The above objectives of improving the performance of ellipsometers as well as adding complex optical surface characteristic measurement capabilities to resonator-based optical systems is achieved in a method and apparatus that incorporate a resonator having intra-resonator reflections that include a surface of interest for measurement or detection purposes. The angle of incidence of the intersection of the intra-resonator reflections with the surface of interest is an angle away from normal, so that polarization changes due to the reflection (including transmission and absorption effects on the reflections) can be measured, and specifically, the ellipsometric parameters, i.e. the complex reflectivity for each of a set of orthogonal polarizations can be measured on the surface of interest. The system can also serve as a polarimeter that yields only the relative magnitude of the reflectivities.

For ellipsometric measurements, light leaving a partially reflective surface of the resonator is detected using two orthogonally-polarized intensity detectors that receive light from two orthogonal polarization states for at least two different effective cavity lengths. The ellipsometric parameters are directly determined from the detected intensities without any additional steps in order to detect the phase difference. The wavelength of the source illuminating the resonator can be swept or the optical length of the cavity can be mechanically or electronically altered. The ellipsometric parameters can then be determined from the position in time of the resonance peaks observed at each detector and the relative amplitudes.

The foregoing and other objects, features, and advantages of the invention will be apparent from the following, more particular, description of the preferred embodiment of the invention, as illustrated in the accompanying drawings, wherein like reference numerals indicate like elements.

DETAILED DESCRIPTION OF ILLUSTRATIVE EMBODIMENT

The above-incorporated patent applications describe various resonator-enhanced optical systems, such as optical storage data and retrieval systems having improved data density, optical measurement systems having improved resolution and contrast, and optical systems having improved detector phase/amplitude slope characteristics controlled over portions of the detector response. The above-recited improvements are developed by placement and tuning of resonators within the optical paths of the associated systems.

When a Fabry-Perot interferometer is adjusted to form an optical resonator, the illumination direction is typically oriented along a direction normal to the two mirrors. Therefore the incidence angle is normal and polarization does not affect the reflectivity, as no polarization change occurs on reflection at normal incidence. The only factor influencing the reflectivity remains the refractive index (the same for both polarizations unless the material is bi-refringent).

In ring resonators and in Fabry-Perot resonators as disclosed in the above-referenced U.S. patent applications, a resonant path having non-normal incidence on a surface of interest is enabled. By employing such a resonator in combination with a detection system that can extract polarization information, a highly sensitive and efficient ellipsometer is provided by the present invention.

The present invention concerns a method and resonator apparatus that provide measurement of the ellipsometric parameters of a surface of interest without requiring a measurement interferometer or a rotating polarizer. By placing the surface of interest within a resonance optical path of a resonator, which may be a Fabry-Perot resonator or another resonator such as a ring resonator, the sharp change in received intensities around resonance for a small change in effective cavity length is easily detected. Therefore, changes in cavity length due to the changes in the complex surface reflectivity for each polarization and orientation direction directly yield the polarization changes in terms of phase and amplitude information for the reflections at the point of intersection of the resonance optical path(s) with the surface of interest.

Figure 1A:
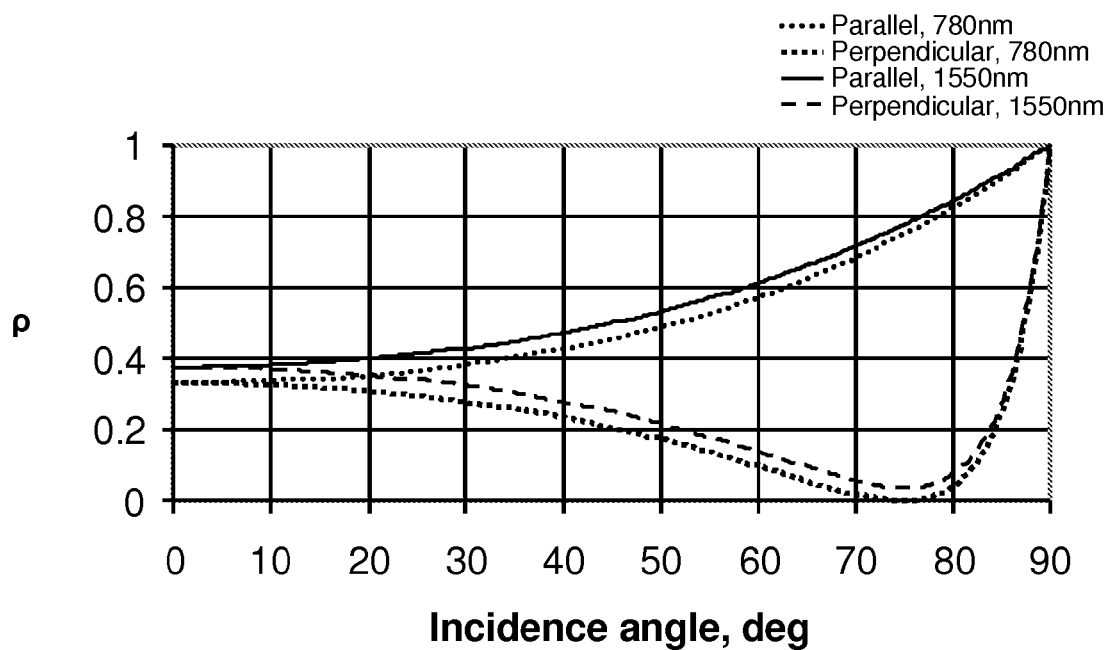
FIG. 1A is a graph showing surface reflectivity of silicon versus angle of incidence.

Referring now to FIG. 1A, the effect of incidence angle on the effective reflectivity of pure silicon is depicted at two wavelengths: 780 nm and 1550 nm. At near grazing incidence, both wavelengths show a reflectivity approaching unity, as is expected. Note that for the parallel polarization case, the sensitivity to incidence angle is much higher than for perpendicular polarization. In the Brewster region or at the Brewster angle, the reflectivity for parallel polarization approaches zero, in this case in the angular region near 75 degrees, while the perpendicular polarization curves show a steadily increasing trend. With the ability to determine transmission/reflection characteristics versus polarization, more information is available not only about the composition and structure of the surface, but also the composition and structure of any foreign objects present on or in a surface of interest. Such measurements when applied to amplitude alone are referred to as polarimetry, but when phase is also determined (i.e., the full complex reflectivity of a surface is measured), the measurements are referred to as ellipsometry. Either type of measurement can be performed in accordance with embodiments of the present invention.

Figure 1B:
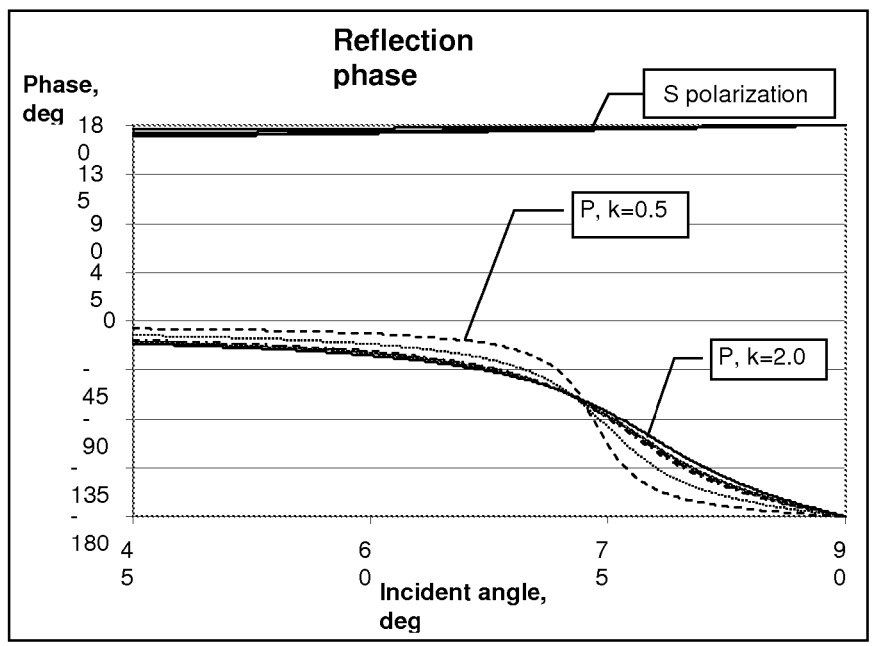
FIG. 1B is a graph showing phase changes due to reflection at a surface versus incidence angle for various refractive indices.

Referring now to FIG. 1B, the effect of incidence angle on reflection phase is shown for both parallel and perpendicular polarizations over a range of refractive indices, where the real part of the refractive index "n" is constant at 3.48, but the imaginary portion "k" varies from 0.5 to 2.0. It should be noted the difference in the signals given by the two polarization directions. In order to measure the phase of the reflection, in prior art systems an interferometer is employed that can determine n, k from relative phase measurements that interfere one reflected polarization with another, and if a reference beam is provided, absolute phase measurement can also be provided. The present invention uses the resonance of the resonator in combination with a special detection system to measure polarization changes due to surface reflection characteristics via amplitude measurements alone. Therefore, no interferometer is required external to the resonator.

Because the polarization change at each reflection contributes to the resonance, the resonant wavelength(s) of the resonator cavity provides information about the reflection phase and polarization changing characteristics at the surface of interest. Depending on the optical system structure, measurement of intensity for each polarization may also be used to determine the surface characteristics in a variety of manners. In essence, the operation of all of the embodiments is uniform in that relative amplitudes for two orthogonal polarizations at a resonance peak reveals the ellipsometric amplitude parameter, and the position of the resonance peaks with respect to the effective cavity length of the resonator yields the ellipsometric phase parameter. The effective cavity length is modulo-2Π ratio of the cavity length to the illumination wavelength.

The embodiments of the invention differ in that some embodiments sweep the wavelength to locate at least two resonance peaks, while others sweep the cavity length via mechanical movement of a reflector or by inserting an electronically-tunable element in the resonance path of the resonator. In general, the sweeping embodiments are the most straightforward as to control and computation, as once the effective cavity is swept over sufficient range and the intensity of the resonator output mapped, the difference in effective cavity length for the multiple resonance points (for the phase measurement mentioned above) can be determined directly from the timing of the resonance peaks. In the non-sweeping cases, it is still necessary to alter the effective cavity length, as multiple resonances must be measured for ellipsometric measurements. Even in polarimetric measurements (amplitude parameter only), the resonance peak of the two polarizations differs with respect to the effective cavity length, so some mechanism must be provided to measure both resonance peaks which generally requires a sweepable or tunable illumination source or cavity.

Figure 2:
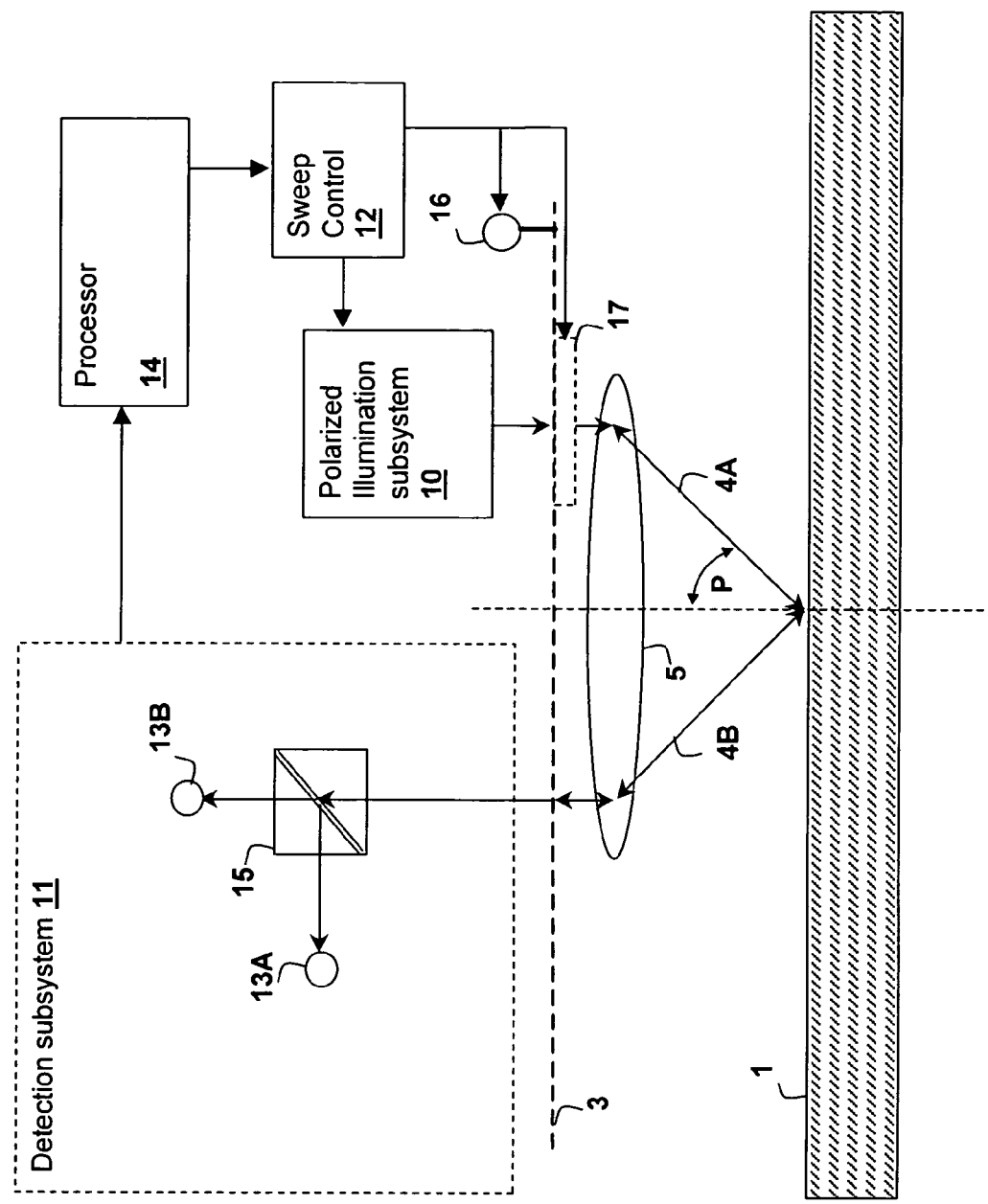
FIG. 2 is a pictorial diagram depicting an optical system in accordance with an embodiment of the invention.

With reference now to the figures, and particularly to FIG. 2, an optical schematic of an optical system in accordance with an embodiment of the invention is illustrated. The system illustrated is a resonant ellipsometer based on a dual reflector Fabry-Perot resonator. In the depicted embodiment, one partially reflective surface 3 provides a first reflector and surface of interest 1 provides the other reflector. However, the resonant path terminates only on partially reflective surface 3 at two distinct locations for each ray, with surface of interest 1 as an intermediate point on the path. The above is accomplished by incorporating a direction changing element (which can alternatively be replaced with two discrete direction-changing single elements) that has a direction-changing characteristic on either side of the point of intersection of rays 4A and 4B with surface of interest 1. A high numerical aperture (high-NA) lens 5 provides the direction-changing element of the depicted embodiment, but other configurations and elements may be substituted as disclosed in the above-referenced U.S. patent applications and as will be illustrated in further detail below.

Lens 5 alters the angular direction of light leaving and striking partially reflective surface 3 from normal incidence at partially reflective surface 3, to an angle P away from normal, so that surface of interest 1 is intersected by rays 4A and 4B at a predetermined angle other than normal. Polarized light is provided by a polarized illumination subsystem 10, and is reflected from surface of interest 1 at the non-normal incidence angle P. The wavelength of the illumination is swept by a sweep control circuit 12 that is controlled by a processor 14 that also receives outputs of a detection subsystem 11 that determines the polarization changes occurring along the resonance path including rays 4A and 4B.

Tuning of the effective cavity length is accomplished by one of three illustrated options. In the first, the illumination source is tuned or swept. A sweep control 12 provides a tuning signal synchronized in timing with processor 14 to polarized illumination subsystem 10. The illumination element may be a semiconductor or tuned-cavity laser. Suitable types of lasers are tunable external cavity lasers (ECL), distributed-feedback (DFB) lasers, distributed Bragg reflector (DBR) lasers and vertical cavity surface emitting lasers (VCSEL). In the second option, the cavity itself is tuned via an electro-mechanical system that moves one of the resonator reflectors. In the illustrated option, a electro-mechanical element 16 such as a piezoelectric crystal/ceramic element or an electromagnetic "voicecoil" or other means is employed to move partially reflective surface 3 to either tune to a resonance peak (via feedback from processor 14) or to sweep through a range of cavity lengths. The third illustrated option is to tune the cavity with an electro-optical element 17 that has electrically tunable optical or mechanical properties. By changing the thickness or refractive index of a material (e.g. an electro-optical liquid or crystal) with an applied voltage, the effective cavity length of the resonator can be tuned or swept.

Detection subsystem 11 is a standard orthogonal polarization detector. A polarizing beam splitter 15 splits the beam transmitted through partially reflective surface 3 at the transmission end of the resonator. The resulting beams (generally representing s and p polarizations) are then provided to individual detectors 13A-B that may be a single point detector such as a photodiode, or may be part of an array such as a CMOS or CCD sensor.

The above-described optical system functions as an ellipsometer without requiring a discrete interferometer or a rotating polarizer. Three data elements are required to completely determine the ellipsometric parameters. It should be understood that the present invention also contemplates systems that do not compute the actual ellipsometric quantities as major/minor axis values, but directly compute some other measure of the complex surface reflection/transmission characteristics such as the n and k values. In theory, as long as two unique values are found, the ellipsometric parameters can be determined. Those values are the ratio of the intensities for each detected polarization at a resonance peak (the s,p amplitude ratio) and the difference in effective cavity length for the two resonance peaks, which gives the phase difference. Only the peak amplitudes are required for polarimetry, where the phase of the polarized and direct reflection are not needed, only their relative amplitudes.

The action of the resonator can be analyzed as follows. Disregarding for the sake of simplicity the effects of the focusing optics and the direction changing elements, i.e. if we assume that the light remains collimated throughout the system and if the incident amplitude is unity, then the transmitted amplitude exiting through partially reflective surface 3 can be calculated as:

$$t_\tau = \tau_1 \rho_x e^{i\Omega} \tau_2 + \tau_1 \rho_x e^{i\Omega} \rho_2 \rho_x e^{i\Omega} \rho_1 \rho_x e^{i\Omega} \tau_2 + \ldots = \tau_1 \rho_x e^{i\Omega} \tau_2 (1 + \rho_2 \rho_1 \rho_x^2 e^{i2\Omega} + \ldots)$$

or $$t_T = \frac{\tau_1 \rho_x e^{i\Omega} \tau_2}{1 - \rho_2 \rho_1 \rho_x^2 e^{i2\Omega}}$$

where $\rho_x$ is the surface reflection amplitude, $\rho_1$, $\rho_2$ and $\tau_1$, $\tau_2$ are the reflection and transmission amplitudes of the two reflections on mirror 3, and $\Omega = 2\pi L/\lambda$, where L is the cavity length (full round-trip through cavity from mirror 3 and back) and $\lambda$ is the wavelength of the illumination.

Assuming for simplicity that $$\rho_1 = \rho_2 = \sqrt{R}, \tau_1 = \tau_2 = \sqrt{T}, \text{ and } \rho_x = e^{i\theta_x}\sqrt{R_x},$$

the transmitted beam is represented by $$t_T = \frac{e^{i(\Omega+\theta_x)}T\sqrt{R_x}}{1 - RR_x e^{i2(\Omega+\theta_x)}}$$

Therefore, the optical parameters of the surface (which determine its reflection amplitude $\rho_x$) have a more complex impact on the detection result when a resonator is present, and ellipsometry in general can be performed with very high sensitivity as will be shown below.

In the vicinity of the resonance, i.e., for $\lambda=\lambda_0+\delta\lambda$ where $\lambda_0$ is the resonant wavelength, the resonant condition dictates that transmitted beam should be maximized in intensity, which occurs when $(\Omega_0+\theta_x)=\pi$ indicating that the round trip through the cavity plus the surface phase change forward and backward is a multiple of the wavelength, so that the resonant rays add in phase.

When illumination subsystem 10 is swept by sweep control 11 the wavelength is swept through the resonance, with detectors 13A-B monitoring the two orthogonal polarization states. The resonances in the multiple polarization states will not occur at the same wavelength and therefore detection peaks will not occur simultaneously, since the condition above gives different resonant cavity phases $\Omega_0$ for different values of reflection phase $\theta_x$. Measuring the time shift between the resonances in two orthogonal polarizations directly yields the ellipsometric parameter $\Delta=\theta_x^{(P)}-\theta_x^{(S)}$ and if the wavelength sweep can be approximated as a linear sweep as $\lambda=\lambda_b+vt$ (where $vt<<\lambda$), then $$\Delta = -\Delta\Omega = \Omega_b v \frac{\Delta t}{\lambda_b} = \frac{2\pi L}{\lambda_b^2} v \cdot \Delta t$$

The ratio of the transmitted intensities at the corresponding resonance peaks (the equivalent of the tangent of the second ellipsometric parameter $\phi$) yields:

$$\tan\Phi = \frac{R_{xP}}{(1-RR_{xP})^2} \cdot \frac{(1-RR_{xS})^2}{R_{xS}}$$
$$= \frac{R_{xP}}{R_{xS}} \cdot \left(\frac{1-RR_{xS}}{1-RR_{xP}}\right)^2$$
$$= \tan\phi \cdot \left(\frac{1-RR_{xS}}{1-RR_{xP}}\right)^2$$

which is just a scaled version of non-resonant parameter $\tan\phi$ multiplied with a "resonator enhancement factor" given by the term $$\left(\frac{1-RR_{xS}}{1-RR_{xP}}\right)^2.$$

The relatively small values of both the nominator and denominator of the enhancement factor make the squared fraction very sensitive to any variation of reflectivity for either of the two polarizations, and consequently the fraction acts as an enhancement factor.

Therefore, the system of FIG. 2 provides a resonator-enhanced optical system that can act as a polarimeter or ellipsometer and provide efficient (due to the swept-wavelength measurement) and highly-sensitive (due to the resonance) ellipsometric performance.

Figure 3C:
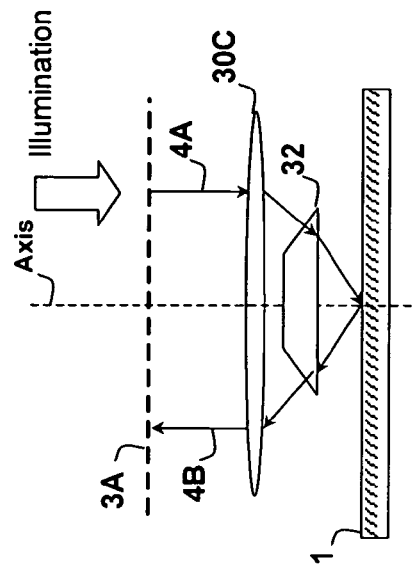
FIGS. 3A-3D are pictorial diagrams depicting dual-reflector optical resonators as are employed in various embodiments of the invention.
Figure 3D:
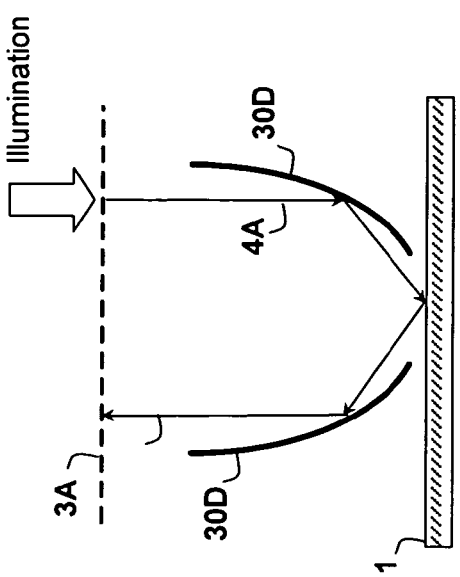
Figure 3A:
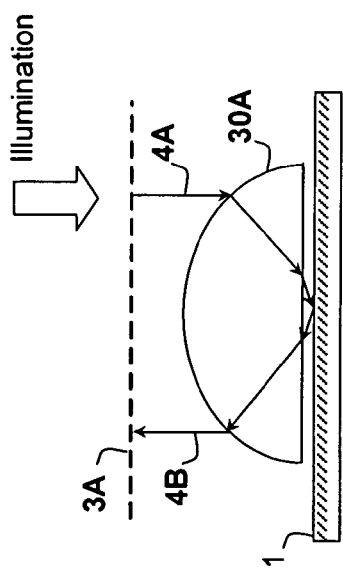
Figure 3B:
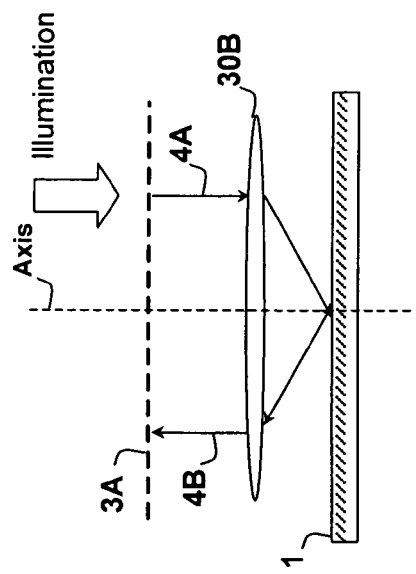

Referring now to FIGS. 3A-3D and particularly to FIG. 3A, elements for implementing the dual-reflector Fabry-Perot resonator of FIG. 2 are illustrated. FIG. 3A depicts a proximity lens that provides a dual direction changing element together with focusing, in a single unit. Rays 4A, 4B are twice bent by the air-lens interfaces and strike surface of interest 1 at an angle close to grazing. FIG. 3B depicts the high numerical aperture (high NA) focusing system 30B positioned between surface of interest 1 and resonator mirror 3A, that may be a lens, a combination of lenses or a mirror configuration that is illuminated off-axis, as shown, so that the angle of incident ray 4A is altered substantially before striking surface of interest 1. However, high-NA focusing system 30B is still operated in the imaging region so that resonance is supported between areas on partially reflective surface 3A and not individual points. Further, polarization effects in high-NA focusing system as with any of the direction changing elements of the present invention must be accounted for. Special coatings may be used to preserve polarization through focusing system 30B.

FIG. 3C depicts a Fabry-Perot resonator including a prism 32 for further increasing an incidence angle of ray 4A on surface of interest 1 that is positioned between focusing system 30C and surface of interest 1. FIG. 3D illustrates a Fabry-Perot resonator constructed with a parabolic mirror 30D used off-axis to provide the direction-changing and focusing elements, and will generally be constructed as a circularly symmetric shell having an aperture for passing light through to surface of interest 1, but could constitute two discrete parabolic mirrors.

In all of the systems described above and all embodiments of the invention, polarization preserving elements and coating are employed to ensure that the ellipsometric performance is not degraded. If a polarization shifting element is employed by design, then a corresponding shift back must be integrated or alternatively accounted for in the design of the detection system, so that polarization state intensities and peak locations are properly employed to determine the ellipsometric parameters.

Figure 4C:
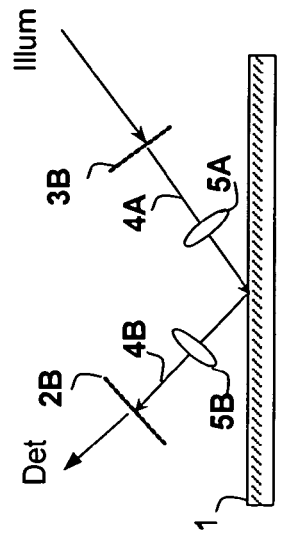
FIGS. 4A-4D are pictorial diagrams depicting triple-reflector optical resonators as are employed in various embodiments of the invention.
Figure 4D:
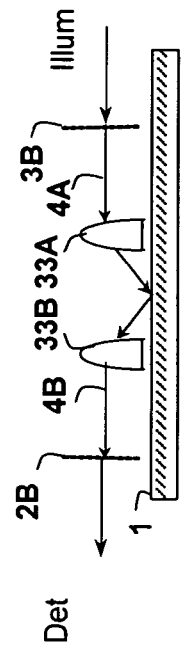
Figure 4A:
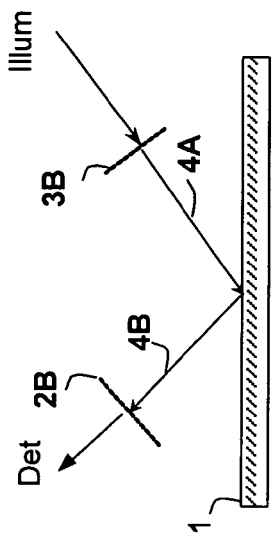
Figure 4B:
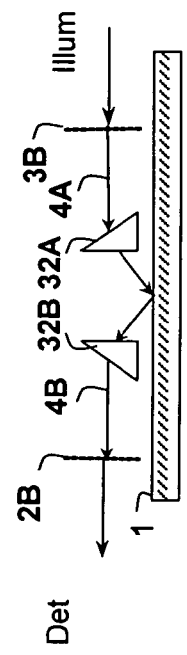

Referring now to FIGS. 4A-4D and particularly to FIG. 4A, elements for implementing a triple-reflector Fabry-Perot resonator that can be used in place of partially-reflective surface 3 and lens 5 of FIG. 2 are illustrated. FIG. 4A depicts a system having two partially reflective surfaces 3B and 2B at ends of a resonant path including incident ray 4A and reflected ray 4B, as described above. Detection is made at an end of the resonator opposing the illuminated end of resonator, also as described above. FIG. 4B illustrates a system including a pair of partially reflective surfaces 2B, 3B oriented in a direction parallel to surface of interest 1 and a pair of prisms 32A, 32B that are provided between partially reflective surfaces 2B, 3B the intersection of rays 4A, 4B, to alter the direction of the light incident on and reflected from surface of interest 1.

FIG. 4C illustrates incorporation of lenses 5A, 5B within the resonator, to increase spatial resolution and decrease sensitivity to the orientation of surface of interest 1. The lenses must be polarization-preserving lenses so that measurements are not distorted or their polarizing properties must be taken into account. Finally, FIG. 4D illustrates a system for providing very near grazing incidence by using a pair of cut convex lenses 33A and 33B to alter the direction of and focus incident ray 4A onto surface of interest 1 and to collimate reflected ray 4B onto exit mirror 2B.

It should be understood for all of the above embodiments that the used of illustrative rays to indicate a resonant path illustrates only a single ray of an image. Incorporation of focusing elements may narrow the profile of the image at a particular surface, but multiple resonant paths exist and the resonance is supported by multiple pairs of points on one or more partially or fully reflected surfaces, as long as the total path length around the resonator is resonant (i.e., an integral number of wavelengths) for that path.

Figure 5:
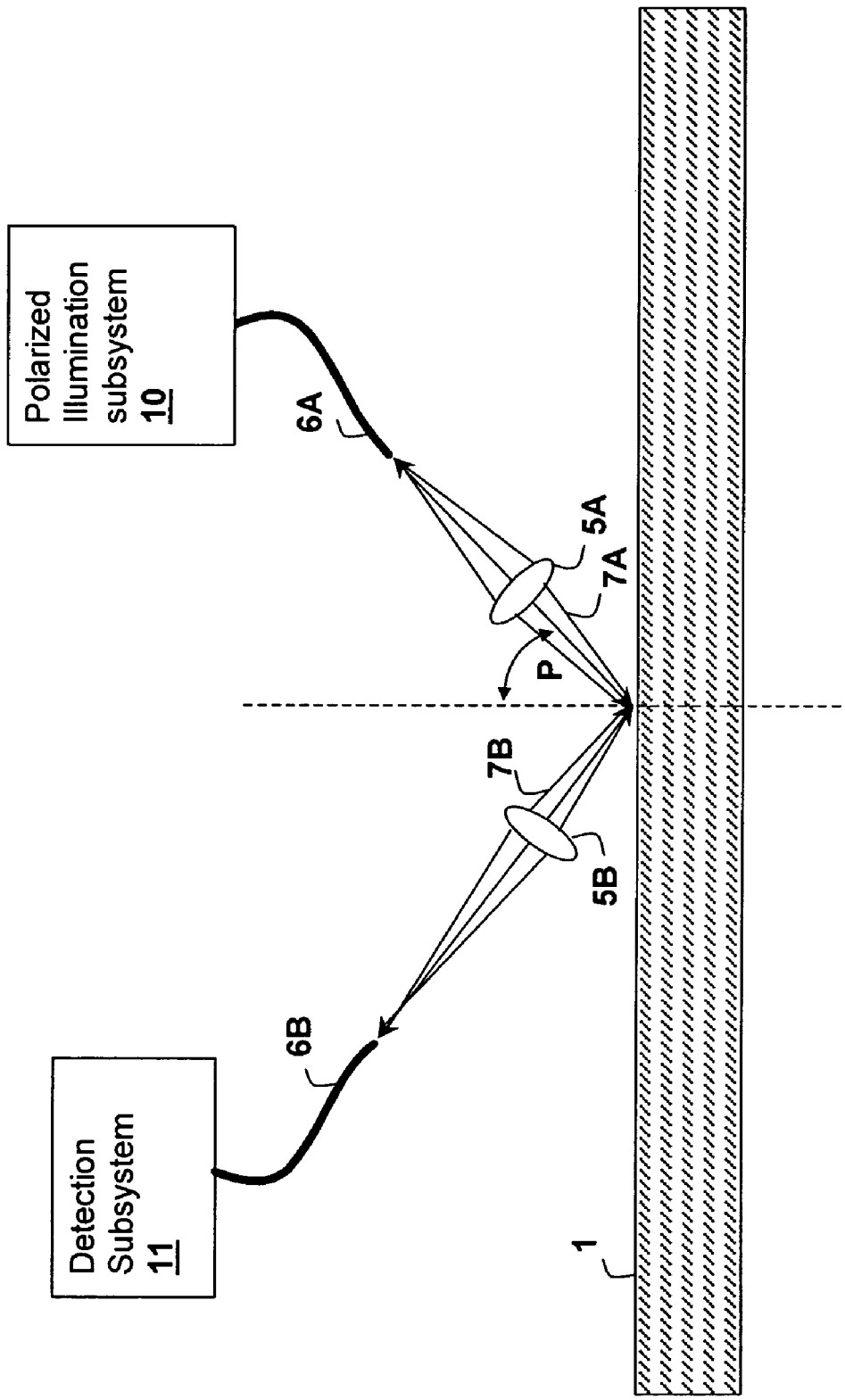
FIG. 5 is a pictorial diagram depicting a triple-reflector optical system in accordance with yet another embodiment of the invention.

Referring now to FIG. 5, an optical system in accordance with another embodiment of the present invention is depicted. The system of FIG. 5 is illustrative of a system in which a point illumination source and a point detector are imaged onto surface of interest 1 by a pair of imaging lenses 5A and 5B (finite conjugation ratio) focused on surface of interest at an angle of incidence other than normal. The point source and point detectors can be provided, as shown, by a pair of polarization-preserving optical fibers 6A, 6B that couple their respective subsystem (illumination subsystem 10B and detection subsystem 11B) directly to the resonator. For clarity in illustration, a polarizing splitter is not illustrated in FIG. 5, but any of the elements known in fiber optic technology to provide polarization splitting can be used in the system, an example of which is provided below with respect to FIG. 6. Optical fibers 6A, 6B have distal ends polished and coated with a partially reflective coating, so that the Fabry-Perot resonator is formed between the faces at the distal ends of optical fibers 6A, 6B. Imaging beams 7A and 7B intersect at a point on surface of interest 1 for which the length is resonant. Any misalignment of the focal axes of imaging lenses 5A and 5B, results only in a shift of the point of intersection of beams 7A and 7B to a point where the resonance is supported.

Illumination subsystem 10 provides a polarized source to illuminate surface of interest 1 through resonator and a detection mechanism to detect changes in intensity of light leaving the resonator, whereby features of surface of interest 1 are measured. Focusing elements 5A, 5B as described above with respect to FIG. 4C are included to focus the light traveling along the resonant paths onto surface of interest 1 to improve the performance of the resonator by de-sensitizing the resonator to angular errors with respect to surface of interest 1.

While the point source/point detector embodiment has disadvantages in that the mirror (fiber end) quality must be very high, the use of such a system is very advantageous in that no collimator is required to produce a small spot size, no separate mirrors are required to form the Fabry-Perot resonator, thus reducing the number of positioning variables in the system. The reduction in complexity and weight is also advantageous for scanning and data storage/retrieval device applications.

Figure 6:
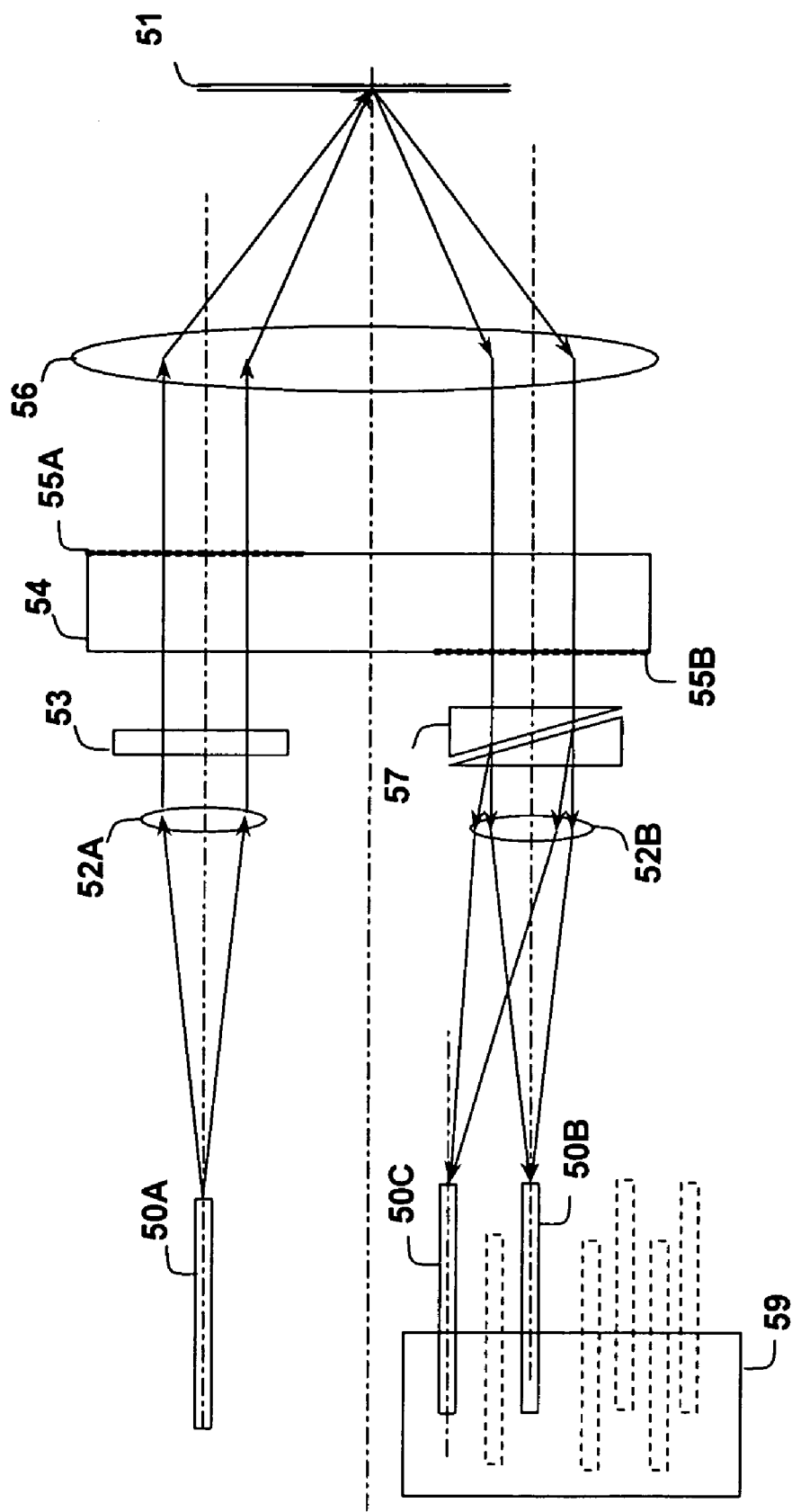
FIG. 6 is a pictorial diagram depicting a dual-reflector optical system in accordance with yet another embodiment of the invention.

Referring now to FIG. 6, an optical system in accordance with yet another embodiment of the present invention is depicted. The depicted embodiment provides for measurement of the ellipsometric (or polarimetric) parameters through multiple angles of incidence, and provides the option of yielding information with respect to discrete angles of incidence on a surface of interest 51. When polarized illumination is provided through polarization-preserving fiber 50A (or alternatively by any fiber with an isolating polarizer at the end between the fiber and the rest of the system, the angle at which a beam exits the transmission side of the resonator (i.e., at partially reflective surface 55B, varies with the surface angle of incidence. As the illumination wavelength is swept or as the resonator is tuned through a range of effective lengths, resonance will occur at a changing angle due to the phase difference induced by the surface upon reflection at that angle. (Another way to describe the operation is that the angle changes to satisfy the zero effective cavity length criteria of resonance.)

Light provided by fiber 50A is collimated by a collimator 52A and is provided to a quarter-wave plate 53 that provide circularly polarized light between quarter wave plate 53 and another quarter wave plate 54 that includes a partially reflective coating 55A forming the first reflector in a Fabry-Perot resonator. High-NA lens 56 (or other focusing system as described above) focuses or images the now linearly-polarized illumination onto a point of surface of interest 51 which reflects the illumination back to high-NA lens 56 at an opposite side. The reflected beam passes again through quarter wave plate 54 and is reflected by a second partially-reflective coating 55B back to the first partially reflective coating 55A forming a resonator. Because each reflection passes twice through the cavity without interfering due to the change of polarization of light by quarter wave plate 54, the effective cavity length is doubled over that of the dual-reflector resonator, which is already doubled over that of a standard Fabry-Perot cavity. The quadrupled cavity length results in a much higher sensitivity than in a standard Fabry-Perot cavity, as described in the above-incorporated co-pending U.S. patent applications.

A birefringent prism 57 splits the beam that is transmitted through second partially reflective coating 55B and out of resonator according to the polarization state of the light, thereby permitting detection of the s and p polarizations. Fiber 50C receives one polarization for a given wavelength and fiber SOB receives the other. Lens 52B focuses the s and p polarization beams separated by birefringent prism 57 onto their respective fibers 50B and 50C, that conduct light back to individual detectors for each of the polarization directions. Since lens 52B focuses any light received within a predetermined angular field to fibers 50B and 50C, the swept-wavelength illumination is integrated at the detectors for the entire range of angle of incidence that occur over the swept-wavelength range due to the phase change at surface of interest 51.

Alternatively, lens 52B can replaced with an array of micro-lenses, one for each fiber in an array/fiber bundle 59 with pairs of fibers/microlenses corresponding to a number of discrete angular orientations (a single micro-lens can feed two fibers positioned at a separation corresponding to the angular separation of the s and p beams leaving birefringent prism 57). Array 59 is then used to detect the ellipsoidal parameters for discrete angles of incidence, which can directly yield the angle of incidence information at surface of interest 51 along with the position of the resonance peak for each polarization and the intensities as the wavelength is swept. It is also possible to implement such a system without micro-lenses at all, using a CCD or CMOS detector array and/or a fiber bundle that directly detects the light leaving birefringent prism at particular angles for each detector element.

The above described architecture illustrates a system that discriminates and determines the ellipsometric parameters for each incidence angle for which a detector pair is provided. The resonance peaks for s,p are discovered and the amplitudes and cavity length differences measured. Sweeping the illumination or tuning the cavity then yields an angular variation of a resonance point corresponding to a changing angle of incidence. In essence, in the depicted embodiment, there is always a pair of s,p detectors detecting resonance peaks and the particular detectors (i.e. particular fibers in the fiber bundles) specify the incidence angle on surface of interest 51 for which resonance is supported at the current effective cavity length.

Figure 7:
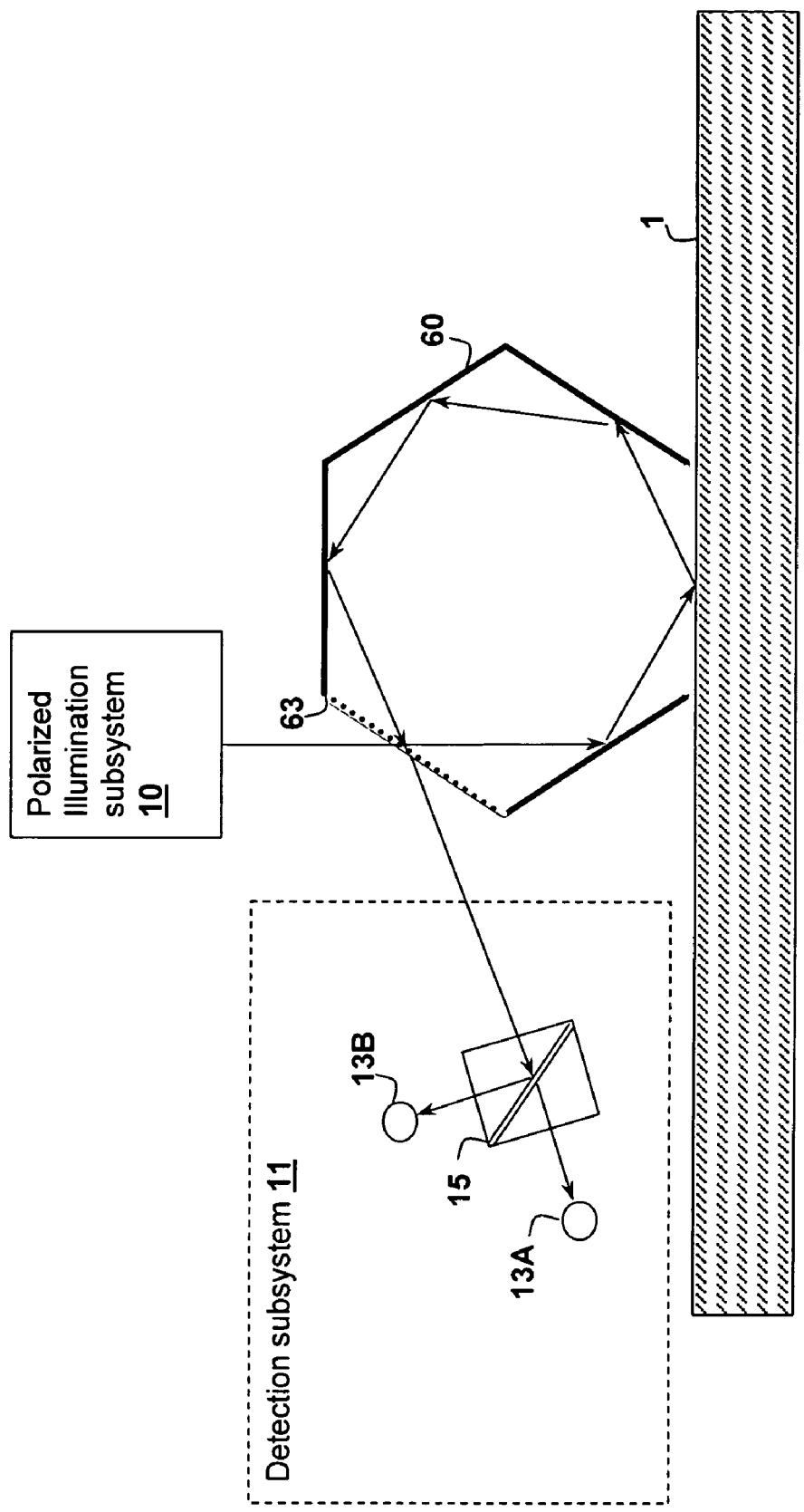
FIG. 7 is a pictorial diagram depicting a ring-resonator optical system in accordance with yet another embodiment of the invention.

Referring now to FIG. 7, an optical system in accordance with yet another embodiment of the present invention is depicted. In the embodiment shown, rather than a Fabry-Perot resonator, a ring resonator is employed. A mirror assembly 60 shown in the form of a hexagonal mirror, but which could be a curved mirror or other order polygon, reflects light between a plurality of reflective faces, at least one partially reflective face 63 for accepting illumination from polarized illumination subsystem 10 and transmitting light to detection subsystem 11 which operates exactly as described above with respect to FIG. 2. One face of mirror assembly 60 is omitted, so that surface of interest 1 forms part of the resonance ring and thus affects the polarization as described above, with some modification to the theoretical expressions recited above to illustrate the behavior of the ring resonator. Mirror assembly must preserve the polarization at each reflection, have a null effect around the ring, or be otherwise compensated for so that the ellipsometric measurements are accurate.

While the invention has been particularly shown and described with reference to the preferred embodiments thereof, it will be understood by those skilled in the art that the foregoing and other changes in form and details may be made therein without departing from the spirit and scope of the invention.

What is claimed is:

1. An optical system, comprising:
    an illumination system for providing a coherent beam for illuminating a surface of interest through a partially reflective surface;
    a resonator comprising a plurality of surfaces including said partially reflective surface and said surface of interest, wherein said resonator illuminates said surface of interest along an incidence angle away from normal in a resonant path of said resonator, and wherein an emitting one of said plurality of surfaces emits light from said resonator;
    a detection system comprising at least two detectors for detecting intensities of light emitted from said resonator, each detector for detecting one of a different polarization of said emitted light; and
    a computation unit for computing polarizing characteristics of said surface of interest at an intersection of said resonant path and said surface of interest in conformity with intensity outputs of said at least two detectors.

2. The optical system of claim 1, wherein said computation unit computes only relative amplitudes of said outputs of said at least two detectors at a resonance peak of said resonator, whereby said optical system functions as a polarimeter.

3. The optical system of claim 1, further comprising means for altering an effective cavity length of said resonator for generating a difference in effective cavity length for at least two resonance peaks, wherein said computation unit determines an ellipsometric amplitude parameter from intensity outputs of said at least two detectors for at least one resonance peak and an ellipsometric phase parameter from said difference in said effective cavity length for said at least two resonance peaks, whereby said optical system functions as an ellipsometer.

4. The optical system of claim 3, wherein said illumination system has a tunable wavelength, whereby said illumination system provides said means for altering an effective cavity length of said resonator by varying a wavelength of said coherent beam.

5. The optical system of claim 4, wherein said illumination system is a tunable laser.

6. The optical system of claim 3, wherein at least a given one of said surfaces of said resonator is mechanically movable, whereby an effective cavity length of said resonator is altered providing said means for altering an effective cavity length of said resonator, and wherein said optical system further comprises an electromechanism for moving said given surface.

7. The optical system of claim 3, and wherein said optical system further comprises an electrically tunable refractive element disposed within said resonator providing said means for altering an effective cavity length of said resonator, whereby an effective cavity length of said resonator is altered.

8. The optical system of claim 1, wherein said illumination source has a sweepable wavelength, and further comprising a control circuit coupled to said illumination source for controlling said wavelength of said illumination source and coupled to said computation unit for providing timing information to said computation unit, and wherein said computation unit stores times of detection of intensity information received from said detection system from each of said at least two detectors and computes time difference between peaks in said intensity information to determine said difference between said effective cavity length of said resonator, whereby said ellipsometric phase parameter is computed.

9. The optical system of claim 1, wherein said resonator has a controllable cavity length, and further comprising a control circuit coupled to said resonator for controlling said cavity length and further coupled to said computation unit for providing timing information to said computation unit, and wherein said computation unit stores times of detection of intensity information received from said detection system from each of said at least two detectors and computes time difference between peaks in said intensity information to determine said difference between said effective cavity length of said resonator, whereby said ellipsometric phase parameter is computed.

10. The optical system of claim 1, wherein said resonator comprises a ring resonator, wherein said surface of interest is a reflector of said ring resonator.

11. The optical system of claim 1, wherein said resonator comprises a Fabry-Perot resonator.

12. The optical system of claim 1, wherein said plurality of surfaces of said resonator comprises:
    a first reflector positioned along a first optical path between said illumination system and said surface of interest; and
    a second reflector positioned on a side opposite said first reflector with respect to an intersection of said first optical path with said surface of interest and in a second optical path between said surface of interest and said second reflector, and wherein primary planes of said first reflector and said second reflector are oriented at angles having a magnitude complementing said incidence angle with respect to said surface of interest.

13. The optical system of claim 12, wherein said first reflector is a polished and coated partially-reflective end of a first optical fiber extending from said illumination system, and wherein said second reflector is a polished and coated partially-reflective end of a second optical fiber extending to said detection system.

14. The optical system of claim 12, further comprising:
a first direction-changing element positioned between said first reflector and said surface of interest for changing a direction of said first optical path from normal to said first reflector to said predetermined nonzero angle; and
a second direction-changing element positioned between said second reflector and said surface of interest for changing a direction of light leaving said surface of interest to a direction normal to said second reflector.

15. The optical system of claim 12, further comprising an optical focusing system positioned along said first optical path between said first reflector and said intersection between said surface of interest and said first optical path, wherein said optical focusing system alters an angle of incidence of said light from said optical path normal to said at least one reflector to a direction aligned along said incidence angle at said surface of interest.

16. The optical system of claim 12, further comprising:
at least one first lens positioned between said first reflector and said surface of interest for focusing light between said first reflector and said surface of interest; and
at least one second lens positioned between second reflector and said surface of interest for collimating light between said surface of interest and said second reflector.

17. The optical system of claim 16, wherein said at least one first lens and said at least one second lens each have a finite conjugation ratio for imaging a point of said surface of interest to corresponding points on said first reflector and said second reflector, respectively.

18. The optical system of claim 16, wherein said first optical path and said second optical path extend along primarily parallel paths to said surface of interest, wherein said first and second lenses have optical axes that are also parallel to the surface of interest but are positioned offset with respect to said first and second optical path, whereby said first lens focuses light travelling from said first reflector to said surface of interest at said predetermined nonzero angle, and wherein said second lens collimates light reflected from said surface of interest onto said second reflector.

19. A method for measuring polarization behavior at a surface of interest, said method comprising:
repeatedly reflecting coherent incident light in a cavity formed at least partially between at least one reflector including at least one partially reflective surface and a surface of interest, so that said light leaves said at least one reflector at a normal angle and intersects said surface of interest at a predetermined nonzero angle other than normal and returns to said at least one reflector in a normal direction;
detecting intensities of light transmitted from said cavity through said at least one partially reflective surface in at least two polarizations, wherein polarization characteristics of said transmitted light have been changed by multiple reflections at a said surface of interest; and
computing an ellipsometric amplitude parameter of said surface of interest from said detected intensities.

20. The method of claim 19, further comprising:
determining a difference between an effective cavity length for at least two peaks in said intensities corresponding to resonances of said reflecting; and
computing an ellipsometric phase parameter of said surface of interest from said detected intensities.

21. An optical system, comprising:
an illumination system for providing a coherent illumination beam;
at least one reflector including at least one partially reflective surface for sustaining multiple internal reflections of said coherent illumination beam in a cavity formed at least partially between said at least one reflector and a surface of interest;
means for directing light leaving said at least one reflector on an optical path normal to said at least one reflector to intersect said surface of interest at a predetermined nonzero angle from normal at said surface of interest and means for returning reflected light from said surface of interest to strike said at least one reflector in a normal direction; and means for determining polarizing characteristics of said surface of interest from only intensity measurements of light transmitted through said at least one partially reflective surface from said cavity.

* * * * *